(12) United States Patent
Kuramoto et al.

(10) Patent No.: US 11,872,326 B2
(45) Date of Patent: Jan. 16, 2024

(54) MEDICAL INSTRUMENT

(71) Applicant: TERUMO KABUSHIKI KAISHA, Tokyo (JP)

(72) Inventors: Masanori Kuramoto, Kanagawa (JP); Narumi Yokote, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 821 days.

(21) Appl. No.: 16/996,017

(22) Filed: Aug. 18, 2020

(65) Prior Publication Data

US 2020/0376171 A1  Dec. 3, 2020

Related U.S. Application Data

(63) Continuation of application No. PCT/JP2019/006073, filed on Feb. 19, 2019.

(30) Foreign Application Priority Data

Feb. 20, 2018  (JP) ................................. 2018-027839

(51) Int. Cl.
*A61L 29/14* (2006.01)
*C08F 220/38* (2006.01)
(Continued)

(52) U.S. Cl.
CPC ............ *A61L 29/14* (2013.01); *A61L 29/041* (2013.01); *A61L 29/043* (2013.01);
(Continued)

(58) Field of Classification Search
None
See application file for complete search history.

(56) References Cited

U.S. PATENT DOCUMENTS

| | | | |
|---|---|---|---|
| 5,997,517 A | 12/1999 | Whitbourne | |
| 2008/0139746 A1* | 6/2008 | Pacetti | A61L 31/16 525/185 |

(Continued)

FOREIGN PATENT DOCUMENTS

| | | |
|---|---|---|
| CN | 101301591 A | 11/2008 |
| CN | 101934101 A | 1/2011 |

(Continued)

OTHER PUBLICATIONS

International Search Report (PCT/ISA/210) dated May 7, 2019, by the Japanese Patent Office as the International Searching Authority for International Application No. PCT/JP2019/006073.
(Continued)

*Primary Examiner* — Fred M Teskin
(74) *Attorney, Agent, or Firm* — BUCHANAN INGERSOLL & ROONEY PC (57) ABSTRACT

Disclosed is a medical device exhibiting superior lubricating property and durability (lubrication retaining property), the medical device comprising a substrate layer, an adhesive layer formed on at least a portion of the substrate layer, comprising a hydrophilic copolymer comprising a structural unit derived from a polymerizable monomer (A) having a sulfobetaine structure, a structural unit derived from a polymerizable monomer (B) having at least one group selected from the group consisting of a sulfonic acid group, sulfuric acid group, sulfurous acid group, and salts thereof, and a structural unit derived from a polymerizable monomer (C) having a photoreactive group, and a surface lubricious layer formed on at least a portion of the adhesive layer, comprising a hydrophilic polymer dissolvable in a solvent capable of dissolving or swelling the hydrophilic copolymer. Also disclosed are methods for producing medical devices
(Continued)

exhibiting superior lubricating property and durability (lubrication retaining property).

20 Claims, 2 Drawing Sheets

(51) Int. Cl.
*A61L 29/04* (2006.01)
*C09J 133/14* (2006.01)

(52) U.S. Cl.
CPC ........ *A61L 29/044* (2013.01); *C08F 220/387* (2020.02); *C09J 133/14* (2013.01); *A61L 2400/10* (2013.01); *A61L 2420/08* (2013.01)

(56) References Cited

U.S. PATENT DOCUMENTS

| | | | |
|---|---|---|---|
| 2011/0274918 A1 | 11/2011 | Omata et al. | |
| 2011/0313077 A1* | 12/2011 | Baba | C08K 5/0008 523/108 |
| 2013/0158488 A1 | 6/2013 | Weaver et al. | |
| 2013/0274367 A1 | 10/2013 | Minagawa et al. | |
| 2015/0105437 A1 | 4/2015 | Tuerk et al. | |
| 2017/0182224 A1* | 6/2017 | Babcock | A61L 29/085 |

FOREIGN PATENT DOCUMENTS

| | | | |
|---|---|---|---|
| CN | 102264402 | A | 11/2011 |
| CN | 103209717 | A | 7/2013 |
| CN | 104152131 | A | 11/2014 |
| CN | 104371131 | A | 2/2015 |
| CN | 105963798 | A | 9/2016 |
| CN | 109641994 | A | 4/2019 |
| JP | H08109221 | A | 4/1996 |
| JP | 2002501788 | A | 1/2002 |
| JP | 2003513712 | A | 4/2003 |
| JP | 2010029688 | A | 2/2010 |
| JP | 2015500088 | A | 1/2015 |
| WO | 2012/032283 | A1 | 3/2012 |
| WO | 2014/099652 | A1 | 6/2014 |
| WO | 2015056611 | A1 | 4/2015 |
| WO | 2016084716 | A1 | 6/2016 |
| WO | 2016158700 | A1 | 10/2016 |
| WO | 2018038063 | A1 | 3/2018 |

OTHER PUBLICATIONS

Written Opinion (PCT/ISA/237) dated May 7, 2019, by the Japanese Patent Office as the International Searching Authority for International Application No. PCT/JP2019/006073.

An English Translation of the International Search Report (Form PCT/ISA/210) and the Written Opinion of the International Searching Authority (Form PCT/ISA/237) dated May 7, 2019, by the Japanese Patent Office in corresponding International Application No. PCT/JP2019/006073. (9 pages).

Gui et al., "Synthesis, Characterization and Flocculation Performance of Zwitterionic Copolymer of Acrylamide and 4-Vinylpyridine Propylsulfobetaine", European Polymer Journal, (Feb. 20, 2009), vol. 45, pp. 1403-1411.

Heath et al., "Design and Characterization of Sulfobetaine-Containing Terpolymer Biomaterials", Acta Biomaterialia (Apr. 11, 2012), vol. 8, pp. 2899-2910.

Li et al., "Syntheses and Properties of the Antifouling Coatings Based on Acrylate Copolymers Containing Zwitterionic Salt", China Coating, (Dec. 2015), vol. 30, No. 12, pp. 52-55 and 60.

Shi et al., "New Handbook of Practical Chemical Formulations", China Building Materials Industry Press, (Nov. 30, 2004), pp. 1494. (3 pages total).

Office Action (The First Office Action) dated Nov. 23, 2021, by the State Intellectual Property Office of People's Republic of China in corresponding Chinese Patent Application No. 201980007330.4 and an English Translation of the Office Action. (16 pages).

Office Action (The Second Office Action) dated Apr. 22, 2022, by the State Intellectual Property Office of People's Republic of China in corresponding Chinese Patent Application No. 201980007330.4 and an English Translation of the Office Action. (13 pages).

* cited by examiner

MEDICAL INSTRUMENT

CROSS-REFERENCES TO RELATED APPLICATIONS

This application is a continuation of International Application No. PCT/JP2019/006073 filed on Feb. 19, 2019, and claims priority to Japanese Application No. 2018-027839 filed on Feb. 20, 2018, the entire content of both of which is incorporated herein by reference.

FIELD OF THE INVENTION

The present disclosure relates to a medical instrument or medical device having a surface lubricious layer exhibiting superior lubricating property and durability (lubrication retaining property).

BACKGROUND DISCUSSION

In recent years, outer diameters of catheters have been reduced to enhance insertion property of a blood vessel into peripheral lesions, and the catheters have been used for diagnosis and treatment of various lesion sites. Therefore, in the diagnosis and treatment with the catheters, this leads to a significant decrease of the clearance between a catheter and the interior surface of a lumen in a living body to cause high frictional resistance on the surface of the catheter. Thus, there is a need for a coating for imparting lubricating property and durability (lubrication retaining property) to a surface of a catheter.

In addition, a substrate of a catheter is formed by using various materials, and thus there are various kinds thereof. For this reason, when a coating is applied on the substrate of the catheter, by providing an adhesive layer between the surface of the substrate and a surface lubricious layer, the catheter is required to cause the surface lubricious layer to be strongly adhered onto the substrate.

For example, U.S. Pat. No. 5,997,517 (also published as Japanese Patent Application Publication No. 2010-029688) discloses a medical device provided with an adhesive layer containing an acrylic resin, an epoxy resin, and an acetal resin as a main component.

SUMMARY

However, in a case where the adhesive layer contains an acrylic resin, an epoxy resin, and an acetal resin as a main component, the surface lubricious layer is worn and the adhesive layer is exposed. Therefore, the coating disclosed in U.S. Pat. No. 5,977,517 cannot sufficiently exhibit lubricating property.

Described herein are embodiments of a medical device exhibiting superior lubricating property (lubricity) and durability (lubrication retaining property).

Also described herein are embodiments of a medical device including an adhesive layer exhibiting sufficient lubricating property and durability (lubrication retaining property) and a surface lubricious layer strongly adhered with the adhesive layer and exhibiting superior lubricating property and durability (lubrication retaining property).

The present inventors have made intensive and extensive studies in view of the observations discussed above and have found that embodiments of a medical device exhibiting superior lubricating properties (lubricity) and durability (lubrication retaining property) can be realized by a medical device including: a substrate layer; an adhesive layer, which is formed on at least a portion of the substrate layer, including a hydrophilic copolymer including a structural unit derived from a polymerizable monomer (A) having a sulfobetaine structure, a structural unit derived from a polymerizable monomer (B) having at least one group selected from the group consisting of a sulfonic acid group ($-SO_3H$), a sulfuric acid group ($-OSO_3H$), a sulfurous acid group ($-OSO_2H$), and groups of salts thereof, and a structural unit derived from a polymerizable monomer (C) having a photoreactive group; and a surface lubricious layer, which is formed on at least a portion of the adhesive layer, including a hydrophilic polymer which can be dissolved in a solvent capable of dissolving or swelling the hydrophilic copolymer.

According to another aspect, a medical device comprises a substrate layer, an adhesive layer formed on at least a portion of the substrate layer, and a surface lubricious layer formed on at least a portion of the adhesive layer. The adhesive layer comprises a hydrophilic copolymer comprising a structural unit derived from a polymerizable monomer (A) having a sulfobetaine structure, a structural unit derived from a polymerizable monomer (B) having at least one group selected from the group consisting of a sulfonic acid group ($-SO_3H$), a sulfuric acid group ($-OSO_3H$), a sulfurous acid group ($-OSO_2H$), and salts thereof, and a structural unit derived from a polymerizable monomer (C) having a photoreactive group. The surface lubricious layer comprises at least one hydrophilic polymer selected from the group consisting of a polymer electrolyte and a polysaccharide.

Another aspect involves a method for producing a medical device that comprises: dissolving a hydrophilic copolymer in a first solvent to prepare a first coating liquid; dissolving a hydrophilic polymer in a second solvent to prepare a second coating liquid; applying the first coating liquid to a surface of a substrate layer of a medical device to form an adhesive layer on the substrate layer; fixing the adhesive layer to the substrate layer via irradiation with ultraviolet rays, electron rays, or gamma rays; applying the second coating liquid to the adhesive layer after the fixing of the adhesive layer to form a surface lubricious layer; and fixing the surface lubricious layer to the substrate layer via irradiation with ultraviolet rays, electron rays, or gamma rays. The hydrophilic copolymer comprises a structural unit derived from a polymerizable monomer (A) having a sulfobetaine structure, a structural unit derived from a polymerizable monomer (B) having at least one group selected from the group consisting of a sulfonic acid group ($-SO_3H$), a sulfuric acid group ($-OSO_3H$), a sulfurous acid group ($-OSO_2H$), and salts thereof, and a structural unit derived from a polymerizable monomer (C) having a photoreactive group. The first and second solvents are each independently selected from the group consisting of water, a lower alcohol, and a mixed solvent of water and a lower alcohol.

DETAILED DESCRIPTION

Set forth below with reference to the accompanying drawings is a detailed description of an exemplary embodiments of a medical device and medical device fabrication method representing examples of the inventive medical device and method disclosed here. The invention is not limited only to the following exemplary embodiments disclosed by way of example. In addition, in the present specification, "X to Y" which represents a range includes X and Y, that is, the phrase means "X or more and Y or less". In addition, unless otherwise specified, operations and measurements of physical properties and the like are made under conditions at room temperature (20° C. to 25° C.) and a relative humidity of 40% RH to 60% RH.

In the present specification, the term "(meth)acryl" includes both of acryl and methacryl. Thus, for example, the term "(meth)acrylic acid" includes both of acrylic acid and methacrylic acid. Similarly, the "(meth)acryloyl" includes both of acryloyl and methacryloyl. Thus, for example, the term "(meth)acryloyl group" includes both of acryloyl group and methacryloyl group.

In addition, in the present specification, unless otherwise defined, the term "substituted" refers to being substituted by a $C_1$ to $C_{30}$ alkyl group, a $C_2$ to $C_{30}$ alkenyl group, a $C_2$ to $C_{30}$ alkynyl group, a $C_1$ to $C_{30}$ alkoxy group, an alkoxycarbonyl group (—COOR, R is a $C_1$ to $C_{30}$ alkyl group), a halogen atom (F, Cl, Br, or I atom), a $C_6$ to $C_{30}$ aryl group, a $C_6$ to $C_{30}$ aryloxy group, an amino group, a $C_1$ to $C_{30}$ alkylamino group, a cyano group, a nitro group, a thiol group, a $C_1$ to $C_{30}$ alkylthio group, or a hydroxyl group. In a case where any group is substituted, it does not include a form of substitution as included in the above definition in which a substituted structure is further substituted. For example, in a case where the substituent is an alkyl group, the alkyl group as the substituent is not further substituted by the alkyl group.

In addition, in the present specification, the term "polymerizable monomer" is simply referred to as "monomer".

In addition, in the present specification, in a case where a structural unit is "derived" from a monomer, it means that the structural unit is a divalent structural unit produced by making a polymerizable unsaturated double bond (C=C) present in a monomer corresponding to the structural unit into a single bond (—C—C—).

The present disclosure provides a medical device including: a substrate layer; an adhesive layer, which is formed on at least a portion of the substrate layer, including a hydrophilic copolymer including a structural unit derived from a polymerizable monomer (A) having a sulfobetaine structure, a structural unit derived from a polymerizable monomer (B) having at least one group selected from the group consisting of a sulfonic acid group (—SO$_3$H), a sulfuric acid group (—OSO$_3$H), a sulfurous acid group (—OSO$_2$H), and groups of salts thereof, and a structural unit derived from a polymerizable monomer (C) having a photoreactive group; and a surface lubricious layer, which is formed on at least a portion of the adhesive layer, including a hydrophilic polymer which can be dissolved in a solvent capable of dissolving or swelling the hydrophilic copolymer. The medical device according to the present disclosure can form a surface lubricious layer exhibiting superior lubricating property and durability (lubrication retaining property). In addition, the adhesive layer including a hydrophilic copolymer according to the present disclosure has good adhesiveness with the substrate layer. In addition, the adhesive layer including a hydrophilic copolymer according to the present disclosure has good adhesiveness with a hydrophilic polymer contained in the surface lubricious layer, and the hydrophilic copolymer itself contained in the adhesive layer exhibit sufficient lubricating property and durability (lubrication retaining property). Therefore, the surface lubricious layer and the adhesive layer are combined to exhibit extraordinarily superior lubricating property and durability (lubrication retaining property).

Hereinafter, preferred exemplary embodiments of the medical device described here will be described with reference to attached figures.

Figure 1:
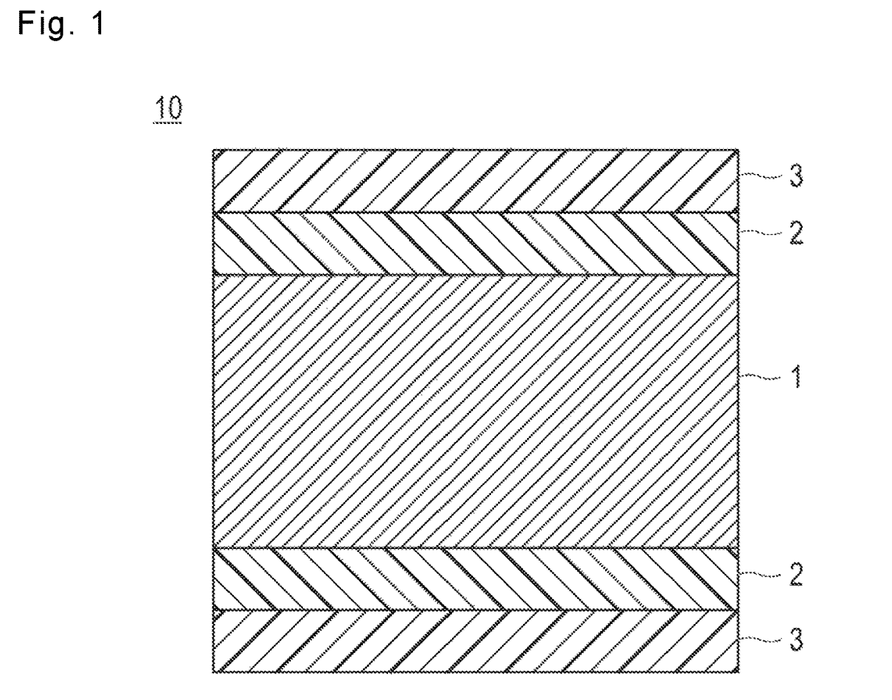
FIG. 1 is a partial cross-sectional view schematically illustrating a surface lamination structure of an exemplary embodiment of a medical device according to embodiments disclosed here.
Figure 2:
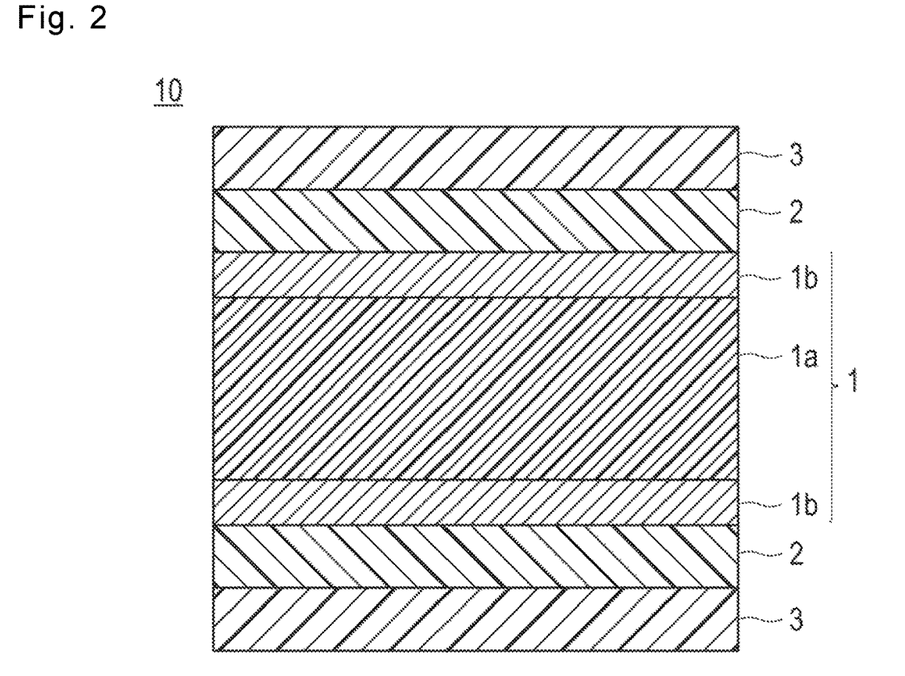
FIG. 2 is a partial cross-sectional view schematically illustrating a different configuration example of a surface lamination structure, as an application example of the exemplary embodiment of FIG. 1.

FIG. 1 is a partial cross-sectional view schematically illustrating a surface lamination structure of an exemplary embodiment of a medical device (hereinafter, simply referred to as "medical device") according to the present disclosure. FIG. 2 is a partial cross-sectional view schematically illustrating a different configuration example of a surface lamination structure, as an application example of the present exemplary embodiment. In FIGS. 1 and 2, 1 denotes a substrate layer, 1a denotes a substrate layer core portion, 1b denotes a substrate surface layer, 2 denotes an adhesive layer, 3 denotes a surface lubricious layer, and 10 denotes a medical device, respectively.

As shown in FIGS. 1 and 2, a medical device 10 of the present exemplary embodiment includes a substrate layer 1, an adhesive layer 2 containing a hydrophilic copolymer fixed so as to coat at least a portion of the surface of the substrate layer 1 (the figure shows an example fixed on the entirety (entire surface) of the substrate layer 1, and a surface lubricious layer 3 containing a hydrophilic polymer fixed so as to coat at least a portion of the surface of the adhesive layer 2 (the figure shows an example fixed on the entirety (entire surface) of the adhesive layer 2 in the figure). The adhesive layer 2 binds to the substrate layer 1 and the surface lubricious layer 3 via a photoreactive group of the hydrophilic copolymer.

Hereinafter, each configuration or aspect of the medical device of this embodiment disclosed by way of example will be described.

<Substrate Layer (Substrate)>

The substrate layer used in the present exemplary embodiment may be configured of any material as long as it reacts with a photoreactive group contained in the hydrophilic copolymer to be described later to form a chemical bond. Specifically, examples of the material configuring (forming) the substrate layer 1 include a metal material, a polymer material, ceramics, and the like. Here, the substrate layer 1 may have a structure in which the entirety (entire surface) of the substrate layer 1 is configured of any of the materials, as shown in FIG. 1, or a substrate surface layer 1b is configured (formed) by coating a surface of a substrate layer core portion 1a configured of any of the material with any of the other material by an appropriate method, as shown in FIG. 2. Examples of the case of the latter include forming a substrate surface layer 1b by coating a surface of the substrate layer core portion 1a formed of a resin material and the like with a metal material by an appropriate method (known methods that may be used include plating, metal deposition, sputtering, and the like); forming a substrate surface layer 1b by coating a surface of the substrate layer core portion 1a formed with a hard reinforcing material such as metal material and ceramic material with a more flexible polymer material than the reinforcing material such as metal material with an appropriate method (known methods that may be used include dipping, spray, and application/printing) or compounding (appropriate reaction treatment) a reinforcing material of a substrate layer core portion 1a and a polymer material of a substrate surface layer 1b; and the like. Therefore, the substrate layer core portion 1a may be a multi-layer structure formed by laminating different materials on multiple layers, or may be a structure (complex) obtained by joining members formed of different materials for each part of a medical device. In addition, another middle layer may be formed between the substrate layer core portion 1a and the substrate surface layer 1b. In addition, the substrate surface layer 1b may be a multi-layer structure formed by laminating different materials on multiple layers, or may be a structure (complex) obtained by joining members formed of different materials for each part of a medical device.

Among the materials configuring (forming) the substrate layer 1, the metal layer is not particularly limited, and a metal material generally used in medical devices such as catheters, stents, and guide wires may be used. Specifically, various stainless steels (SUS) such as SUS304, SUS316, SUS316L, SUS420J2, and SUS630, gold, platinum, silver, copper, nickel, cobalt, titanium, iron, aluminum, or tin, or nickel-titanium (Ni—Ti) alloy, nickel-cobalt (Ni—Co) alloy, cobalt-chrome (Co—Cr) alloy, and Zinc-tungsten (Zn—W) alloy, and the like are examples. These may be used alone, or may be used in combination of two or more thereof. For the metal material, an optimal metal material may be appropriately selected as a substrate layer such as catheter, stent, and guide wire which is a use.

In addition, among the material configuring (forming) the substrate layer 1, the polymer material is not particularly limited, and a polymer material generally used in medical devices such as catheters, stents, and guide wire is used. Specifically, examples thereof include polyamide resin, polyolefin resin such as polyethylene such as straight chain low-density polyethylene (LLDPE), low-density polyethylene (LDPE), high-density polyethylene (HDPE), and modified polyethylene and polypropylene, polyester resin such as polyethylene terephthalate, styrole resin such as polystyrene, cyclic polyolefin resin, modified polyolefin resin, epoxy resin, urethane resin, diaryl phthalate resin (aryl resin), polycarbonate resin, fluororesin, amino resin (urea resin, melamine resin, benzoguanamine resin), acrylic resin, polyacetal resin, vinyl acetate resin, phenol resin, vinyl chloride resin, silicon resin, polyether resin such as polyetherether ketone (PEEK), polyimide resin, and the like, and from a viewpoint of adhesiveness with an adhesive layer to be described later, polyethylene such as high-density polyethylene (HDPE) and modified polyethylene, polyether resin such as polyetherether ketone (PEEK), and polyamide resin are preferable. These may be used alone, or may be used in combination of two or more thereof. For the polymer material, an optimal polymer material may be appropriately selected as a substrate layer such as a catheter, stent, or guide wire.

In addition, a shape of the substrate layer is not particularly limited, and a sheet shape, a line or linear shape (wire), a tubular shape, and the like may be selected based on the intended use.

<Adhesive Layer (Hydrophilic Copolymer)>

The hydrophilic copolymer contained in the adhesive layer according to embodiments disclosed by way of example may contain structural units derived from a polymerizable monomer (A) having a sulfobetaine structure (hereinafter, also referred to as "monomer A"); structural units derived from a polymerizable monomer (B) having at least one group selected from the group consisting of a sulfonic acid group ($-SO_3H$), a sulfuric acid group ($-OSO_3H$), a sulfurous acid group ($-OSO_2H$), and groups of salts thereof (hereinafter, also referred to as "monomer B"); and structural units derived from a polymerizable monomer (C) having a photoreactive group (hereinafter, also referred to as "monomer C"). The hydrophilic copolymer can form an adhesive layer exhibiting sufficient lubricating property and durability (lubrication retaining property). In addition, the hydrophilic copolymer has good adhesiveness with the substrate layer and a hydrophilic polymer which can be dissolved in a solvent capable of dissolving or swelling the hydrophilic copolymer to be described later. The mechanism of causing the exemplary effects has not been completely understood, but the following mechanism is supposed.

The photoreactive group contained in a structural unit derived from the monomer C may produce a reactive species by irradiation with an active energy ray, and may react with a substrate layer surface and a hydrophilic polymer which can be dissolved in a solvent dissolving or swelling the hydrophilic copolymer to be described later to form a chemical bond. Thus, an adhesive layer containing the hydrophilic copolymer according to the present disclosure is strongly fixed on a substrate layer to strongly fix a surface lubricious layer, thereby exhibiting superior durability (lubrication retaining property).

The mechanism is merely an assumption, and the present disclosure is not limited to this assumption.

As long as the lubricating property (lubricity) and durability (lubrication retaining property) are not affected, another layer may be provided between the adhesive layer and the substrate layer, but the adhesive layer is preferably positioned immediately above the substrate layer such that the adhesive layer and substrate layer are in immediate or direct contact.

Hereinafter, each polymerizable monomer configuring the hydrophilic copolymer contained in the adhesive layer will be described.

[Polymerizable Monomer]

(Polymerizable Monomer A)

The polymerizable monomer A (monomer A) is a polymerizable monomer having a sulfobetaine structure. The sulfobetaine structure contained in a structural unit derived from the monomer A has a superior lubricating property imparting effect. Thus, the hydrophilic copolymer having a structural unit derived from the monomer A is considered to have superior lubricating property. In addition, a homopolymer of the monomer A can be dissolved in an NaCl aqueous solution, but does not dissolve or hardly dissolves in water or lower alcohols. Thus, a possibility of higher electrostatic interaction of sulfobetaine structures is suggested. Thus, a strong cohesive force is caused inside the adhesive layer containing the hydrophilic copolymer according to the present disclosure. Accordingly, the adhesive layer is considered to have high strength (superior durability). The above description is an assumption, and the present disclosure is not limited to the assumption.

The "sulfobetaine structure" as used herein refers to a structure where a positive charge and a negative charge containing a sulfur element are present at positions that are not adjacent to each other, an atom having a positive charge has no hydrogen atom that can be released, and the total sum of the charges is zero.

Examples of the monomer A include, but are not limited to, compounds represented by the following general formulae.

In the above general formulae, $R^a$ and $R^d$ may each independently be an alkylene group having 1 to 30 carbon atoms which may be substituted or an arylene group having 6 to 30 carbon atoms which may be substituted, $R^b$ and $R^c$ may each independently be an alkyl group having 1 to 30 carbon atoms which may be substituted or an aryl group having 6 to 30 carbon atoms which may be substituted, and Y may be an ethylenically unsaturated group, such as an acryloyl group ($CH_2$=CH—C(=O)—), a methacryloyl group ($CH_2$=C($CH_3$)—C(=O)—), or a vinyl group ($CH_2$=CH—). In the general formulae, the total sum of positive charges and negative charges is zero.

Examples of arylene groups having 1 to 30 carbon atoms include a methylene group, an ethylene group, a trimethylene group, a propylene group, an isopropylene group, a butylene group, an isobutylene group, a sec-butylene group, a tert-butylene group, and a pentylene group.

Examples of arylene groups having 6 to 30 carbon atoms include a phenylene group, a naphthylene group, an anthracenylene group, a phnanthrenylene group, a pyrenylene group, a perylenylene group, a fluorenylene group, and a biphenylene group.

Examples of alkyl groups having 1 to 30 carbon atoms include a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, a neopentyl group, and an n-hexyl group.

Examples of aryl groups having 6 to 30 carbon atoms include a phenyl group, a biphenyl group, a terphenyl group, a pentalenyl group, an indenyl group, a naphthyl group, an azulenyl group, a heptalenyl group, and a biphenylenyl group.

Among them, the monomer A can be a compound represented by the following formula (1) from the viewpoint of further enhancement of lubricating property and durability (lubrication retaining property).

In the formula (1), $R^{11}$ is a hydrogen atom or a methyl group.

In addition, $Z^1$ is an oxygen atom (—O—) or —NH—, and an oxygen atom (—O—) is preferable.

In addition, in the formula (1), $R^{12}$ and $R^{15}$ are each independently a straight chain or branched chain alkylene group having 1 to 20 carbon atoms from the viewpoint of further enhancement of lubricating property and durability (lubrication retaining property), for example, a straight chain or branched chain alkylene group having 1 to 12 carbon atoms, for example, a straight chain or branched chain alkylene group having 1 to 8 carbon atoms, for example, a straight chain or branched chain alkylene group having 1 to 6 carbon atoms, for example, a straight chain alkylene group having 1 to 3 carbon atoms (a methylene group, an ethylene group, or a trimethylene group).

In the formula (1), $R^{13}$ and $R^{14}$ are each independently a straight chain or branched chain alkyl group having 1 to 20 carbon atoms from the viewpoint of further enhancement of lubricating property and durability (lubrication retaining property), for example, a straight chain or branched chain alkyl group having 1 to 12 carbon atoms, for example, a straight chain or branched chain alkyl group having 1 to 8 carbon atoms, for example, a straight chain or branched chain alkyl group having 1 to 4 carbon atoms, for example, a methyl group.

Examples of compounds represented by the formula (1) include {2-[meth]acryloyloxy}ethyl}dimethyl-(3-sulfopropyl)ammonium hydroxide, {2-[(meth)acryloyloxy]ethyl}dimethyl-(2-sulfoethyl)ammonium hydroxide, {2-[(meth)acryloyloxy]ethyl}diethyl-(2-sulfoethyl)ammonium hydroxide, {2-[(meth)acryloyloxy]ethyl}diethyl-(3-sulfopropyl)ammonium hydroxide, {3-[(meth)acryloyloxy]propyl}dimethyl-(2-sulfoethyl)ammonium hydroxide, {3-[(meth)acryloyloxy]propyl}diethyl-(3-sulfopropyl) ammonium hydroxide, {3-[(meth)acryloyloxy]propyl}diethyl-(2-sulfoethyl)ammonium hydroxide, and {3-[(meth)acryloyloxy]propyl}diethyl-(3-sulfopropyl) ammonium hydroxide, and among them, {2-[(meth) acryloyloxy]ethyl}dimethyl-(3-sulfopropyl)ammonium hydroxide is preferable. The above compounds may be used alone or in combination of two or more thereof.

The monomer A may be either of a synthetic compound or a commercially available product. A commercially available product is available from Sigma-Aldrich Co. LLC., for example. In addition, an exemplary compound may be synthesized in view of A. Laschewsky, Polymers, 6, 1544-1601 (2014), for example.

In addition, the monomer A is not limited to the compound represented by the aforementioned general formulae, and may be a compound that has a form having a positive charge at an end thereof.

In the hydrophilic copolymer, the content of the structural units derived from the monomer A, based on 100% by mole of the total of the structural units derived from all monomers, is preferably 0.1% to 99% by mole, more preferably 1% to 99% by mole, further more preferably 5% to 99% by mole, and particularly preferably 10% to 99% by mole. In such a range, a good balance between the lubricating property and the solvent solubility can be achieved. The molar percentage can be substantially equal to the proportion of the amount (moles) of the monomer A supplied based on the total amount (moles) of all the monomers supplied in production of the polymer.

(Polymerizable Monomer B)

The polymerizable monomer B (monomer B) is a polymerizable monomer having at least one group selected from the group consisting of a sulfonic acid group (—SO$_3$H), a sulfuric acid group (—OSO$_3$H), a sulfurous acid group (—OSO$_2$H), and groups of salts thereof. With such a group incorporated, anionization occurs in an aqueous solvent, and electrostatic repulsion can occur between hydrophilic copolymer molecules. As a result, electrostatic interaction between sulfobetaine structures between hydrophilic copolymers and hydrophobic interaction between hydrophilic copolymers are decreased. Thus, the solvent solubility of the copolymer can be enhanced. This effect of enhancement can be particularly notable when the photoreactive group in the monomer C is a benzophenone group. The benzophenone group has a plurality of aromatic rings, and thus is easily associated by π-π interaction. A polymer containing the benzophenone group aggregates and is easy to become non-soluble. However, by incorporating structural units derived from the monomer B, electrostatic repulsion occurs as described above and association of benzophenone groups is suppressed, and therefore the solubility or the dispersibility of the polymer is considered to be dramatically enhanced. The mechanism described above is an assumption, and embodiments described herein are not limited to this assumption. Alternatively, also when the monomer C contains an ester group, the above effect of enhancement can be obtained as well. In addition, the monomer B preferably also has an ethylenically unsaturated group such as a (meth) acryloyl group, a vinyl group, or an aryl group.

Among them, from the viewpoint of further enhancement of the solvent solubility, the monomer B is preferably a compound represented by the following formula (2), (3), or (4), and more preferably a compound represented by the following formula (2).

(2)

In the formula (2), R$^{21}$ is a hydrogen atom or a methyl group. In addition, Z$^2$ is an oxygen atom (—O—) or —NH—, and preferably —NH—.

In the formula (2), from the viewpoint of further enhancement of the solvent solubility, R$^{22}$ is a straight chain or branched chain alkylene group having 1 to 20 carbon atoms, preferably a straight chain or branched chain alkylene group having 1 to 12 carbon atoms, more preferably, a straight chain or branched chain alkylene group having 1 to 8 carbon atoms, further more preferably a straight chain or branched chain alkylene group having 1 to 6 carbon atoms, and particularly preferably a branched chain alkylene group having 3 to 5 carbon atoms. The branched chain alkylene group having 3 to 5 carbon atoms is a group represented by —CH(CH$_3$)—CH$_2$—, —C(CH$_3$)$_2$—CH$_2$—, —CH(CH$_3$)—CH(CH$_3$)—, —C(CH$_3$)$_2$—CH$_2$—CH$_2$—, —CH(CH$_3$)—CH(CH$_3$)—CH$_2$—, —CH(CH$_3$)—CH$_2$—CH(CH$_3$)—, —CH$_2$—C(CH$_3$)$_2$—CH$_2$—, and —C(CH$_3$)$_2$—CH(CH$_3$)— (provided that the order of linking of the above group in the formula (2) is not limited), and among them, a group represented by —C(CH$_3$)$_2$—CH$_2$— is particularly preferable.

In the formula (2), X is a group selected from the group consisting of a sulfonic acid group (—SO$_3$H), a sulfuric acid group (—OSO$_3$H), a sulfurous acid group (—OSO$_2$H), and salts thereof, and from the viewpoint of the degree of acid dissociation (that is, the degree of easiness of anionization) and in turn the solvent solubility of the copolymer, X is preferably a group selected from the group consisting of a sulfonic acid group, a sulfuric acid group, and salts thereof, and in terms of the availability of the monomer, X is more preferably a sulfonic acid group or a group of a salt thereof. Here, the salt is not particularly limited, and examples thereof include an alkali metal salt (sodium salt, potassium salt, and the like).

Examples of the compounds represented by the formula (2) include 2-(meth)acrylamide-2-methyl-1-propane-sulfonic acid, 1-[(meth)acryloyloxymethyl]-1-propanesulfonic acid, 2-[(meth)acryloyloxy]-2-propanesulfonic acid, 3-[(meth)acryloyloxy]-1-methyl-1-propanesulfonic acid, 2-sulfoethyl(meth)acrylate, 3-sulfopropyl(meth)acrylate, and salts thereof. The compounds may be used alone or in combination of two or more thereof.

The compound represented by the formula (2) used may be either of a synthetic compound or a commercially available product, and a commercially available product may be available, for example, from Tokyo Chemical Industry, Co., Ltd.

(3)

In the formula (3), R$^{31}$ is a hydrogen atom or a methyl group.

In the formula (3), R$^{32}$ is a single bond or a straight chain or branched chain alkylene group having 1 to 20 carbon atoms, preferably a single bond or a straight chain or branched chain alkylene group having 1 to 12 carbon atoms, more preferably a single bond or a straight chain or branched chain alkylene group having 1 to 8 carbon atoms, further more preferably a single bond or a straight chain or branched chain alkylene group having 1 to 4 carbon atoms, and particularly preferably a single bond. Examples of alkylene groups here are the same as in the formula (2) and therefore the description is omitted here.

In the formula (3), X is a group selected from the group consisting of a sulfonic acid group (—SO$_3$H), a sulfuric acid group (—OSO$_3$H), a sulfurous acid group (—OSO$_2$H), and groups of salts thereof, and from the viewpoint of the degree of acid dissociation (that is, the degree of easiness of anionization) and in turn the solvent solubility of the copolymer, X is preferably a group selected from the group consisting of a sulfonic acid group and a sulfuric acid group, and groups of salts thereof, and in terms of the availability of the monomer, X is more preferably a sulfonic acid group or groups of salts thereof.

Examples of compounds represented by the formula (3) include vinylsulfonic acid, 2-propene-1-sulfonic acid, 2-methyl-2-propene-1-sulfonic acid, and salts thereof. The compounds may be used alone or in combination of two or more thereof.

The compound represented by the formula (3) used may be either of a synthetic compound or a commercially available product, and a commercially available product may be available from, for example, Asahi Kasei Finechem Co., Ltd., or Tokyo Chemical Industry Co., Ltd (for example, 2-methyl-2-propene-1-sulfonic acid sodium salt).

(4)

In the formula (4), $R^{41}$ is a hydrogen atom or a methyl group.

In the formula (4), $R^{42}$ is a straight chain or branched chain alkylene group having 1 to 20 carbon atoms, preferably a straight chain or branched chain alkylene group having 1 to 12 carbon atoms, more preferably a straight chain or branched chain alkylene group having 1 to 8 carbon atoms, and further more preferably a straight chain or branched chain alkylene group having 1 to 6 carbon atoms. Examples of alkylene groups here are the same as in the formula (2), and therefore the description is omitted here.

In the formula (4), X is a group selected from the group consisting of a sulfonic acid group (—SO$_3$H), a sulfuric acid group (—OSO$_3$H), a sulfurous acid group (—OSO$_2$H), and groups of salts thereof, and from the viewpoint of the degree of acid dissociation (that is, the degree of easiness of anionization) and in turn the solvent solubility of the copolymer, X is preferably a group selected from the group consisting of a sulfonic acid group, a sulfuric acid group, and groups of salts thereof, and in terms of the availability of the monomer, X is more preferably a sulfonic acid group or a group of a salt thereof.

Examples of compounds presented by the formula (4) include 2-sulfoxyethyl vinyl ether, 3-sulfoxy-n-propyl vinyl ether, and salts thereof. The compounds may be used alone or in combination of two or more thereof.

The compound represented by the formula (4) used may be either of a synthetic compound or a commercially available product.

In the hydrophilic copolymer, the content of the structural units derived from the monomer B based on 100% by mole of the total of the structural units derived from all monomers is preferably 0.1% to 99% by mole, more preferably 0.2% to 99% by mole, further more preferably 0.5% to 99% by mole, and particularly preferably 1 to 99% by mole. In this range, a good balance of the lubricating property and the solvent solubility can be achieved. The molar percentage can be substantially equal to the proportion of the amount (moles) of the monomer B supplied based on the total amount (moles) of all the monomers supplied in production of the polymer.

(Polymerizable Monomer C)

The polymerizable monomer C (monomer C) is a polymerizable monomer having a photoreactive group. As used herein, the "photoreactive group" refers to a group that generates a reactive species, such as a radical, a nitrene, or a carbene when irradiated with an active energy ray, and can react with a substrate layer (resin) or a surface lubricious layer (hydrophilic polymer) to form a chemical bond. Thus, an adhesive layer containing the hydrophilic copolymer can be strongly fixed on a surface of the substrate layer or the surface lubricious layer. Accordingly, by disposing the adhesive layer between the substrate layer and the surface lubricious layer, the medical device can exhibit sufficient durability (lubrication retaining property). In addition, the monomer C can have, in addition to the photoreactive group, an ethylenically unsaturated group such as a (meth)acryloyl group, a vinyl group, or an allyl group.

Examples of photoreactive groups include an azide group, a diazo group, a diazirine group, a ketone group, and a quinone group.

Examples of azide groups include aryl azide groups, such as phenyl azide and 4-fluoro-3-nitrophenyl azide; acyl azide groups, such as benzoyl azide and p-methylbenzoyl azide; azideformate groups, such as ethyl azide formate and phenyl azideformate; sulfonyl azide groups, such as benzenesulfonyl azide; and phosphoryl azide groups, such as diphenylphosphoryl azide and diethylphosphoryl azide.

Examples of diazo groups include groups derived from, for example, diazoalkanes, such as diazomethane and diphenyldiazomethane; diazoketones, such as diazoacetophenone and 1-trifluoromethyl-1-diazo-2-pentanone; diazoacetates, such as t-butyl diazoacetate and phenyl diazoacetate; and β-keto-α-diazoacetoacetates, such as t-butyl-α-diazoacetoacetate.

Examples of diazirine groups include groups derived from, for example, 3-trifluoromethyl-3-phenyldiazirine.

Examples of ketone groups include groups having a structure, such as acetophenone, benzophenone, anthrone, xanthine, or thioxanthone.

Examples of quinone groups include groups derived from, for example, anthraquinone.

The photoreactive group can be appropriately selected according to the type of the substrate layer of the medical device, and the like. For example, when the substrate layer is formed of a polyolefin resin, such as polyethylene resin, a polyamide resin, a polyurethane resin, a polyester resin, or the like, the photoreactive group can be a ketone group or a phenyl azide group, and in terms of the availability of the monomer, it can be a group having a benzophenone structure (a benzophenone group).

Examples of the monomer C include 2-azidoethyl(meth)acrylate, 2-azidopropyl(meth)acrylate, 3-azidopropyl(meth)acrylate, 4-azidobutyl(meth)acrylate, 4-(meth)acryloyloxybenzophenone, 4-(meth)acryloyloxyethoxybenzophenone, 4(meth)acryloyloxy-4'-methoxybenzophenone, 4-(meth)acryloyloxy-4-bromobenzophenone, 4-(meth)acryloyloxyethoxy-4'-bromobenzophenone, 4-styrylmethoxybenzophenone, and 4-(meth)acryloyloxythioxanthone.

The monomer C used may be either of a synthetic compound or a commercially available product, and a commercially available product may be available, for example, from MRC UNITEC Co., Ltd.

In the hydrophilic copolymer, the content of the structural units derived from the monomer C based on 100% by mole of the total of the structural units derived from all monomers is preferably 0.1% to 40% by mole, more preferably 0.1% to 30% by mole, further more preferably 0.1% to 25% by mole, and particularly preferably 0.1% to 20% by mole.

In the molar ranges described above, the hydrophilic copolymer can sufficiently bind to the substrate layer (resin) or the surface lubricious layer (hydrophilic polymer), and therefore the adhesive layer containing the hydrophilic copolymer can be strongly fixed to the substrate layer or the surface lubricious layer. In addition, in these ranges, sufficient amounts of the other monomers (the monomers A and B) can exist, and therefore the hydrophilic copolymer can be effectively improved in the lubricating property and durability by the monomer A and the solvent solubility by the monomer B. The molar percentage can be substantially equal to the proportion of the amount (moles) of the monomer C supplied based on the total amount (moles) of all the monomers supplied in production of the polymer.

The hydrophilic copolymer may contain any structural units derived from other polymerizable monomers than the monomer A, the monomer B, and the monomer C (hereinafter also referred to as "other monomers"). In the hydrophilic copolymer of the present disclosure, the content of the structural units derived from other monomers, based on 100% by mole of the total amount of structural units derived from all the monomer, is preferably less than 10% by mole, more preferably less than 5% by mole, and further more preferably less than 1% by mole (lower limit: 0% by mole). The hydrophilic copolymer of the present disclosure preferably consists of the monomer A, the monomer B, and the monomer C. The molar percentage can be substantially equal to the proportion of the amount (moles) of the other monomers supplied based on the total amount (moles) of all the monomers supplied in production of the polymer.

The ends of the hydrophilic copolymer are not particularly limited and can be appropriately defined according to the type of the material used, but are generally hydrogen atoms. The structure of the copolymer is also not particularly limited, and may be any of a random copolymer, an alternating copolymer, a periodical copolymer, and a block copolymer.

A weight average molecular weight (Mw) of the hydrophilic copolymer is preferably several thousands to several millions, more preferably 1,000 to 1,000,000, and particularly preferably 5,000 to 500,000. The "weight average molecular weight" described here is a value measured by gel permeation chromatography (GPC) using polyethylene glycol as a standard.

[Method of Producing Hydrophilic Copolymer]

The method of producing the hydrophilic copolymer is not particularly limited, and known polymerization methods, such as radical polymerization, anion polymerization, and cation polymerization may be adopted, and radical polymerization, which allow for easy production, is preferably used.

An example of a polymerization method includes a method in which the monomer A, the monomer B, the monomer C, and other monomers depending on the necessity, are copolymerized by stirring and heating them together with a polymerization initiator in a polymerization solvent.

The polymerization temperature is not particularly limited, but is preferably 25° C. to 100° C. and more preferably 30° C. to 80° C. The polymerization time is not particularly limited, but is preferably 30 minutes to 24 hours and more preferably 1 to 8 hours.

The polymerization solvent is an aqueous solvent such as water; and alcohols, such as methanol, ethanol, propanol, n-butanol, and 2,2,2-trifluoroethanol. From the viewpoint of dissolving raw materials used in the polymerization, one of the solvents may be used alone or two or more thereof may be used in combination.

The concentration of the polymerizable monomers is not particularly limited, but is preferably 0.05 to 1 g/mL and more preferably 0.1 to 0.5 g/mL in terms of the total solid amount (g) of various polymerizable monomers relative to the polymerization solvent (mL). In addition, proportions of the amount (moles) of each monomer supplied based on the total amount (moles) of all the monomers supplied can be as described above.

The reaction solution containing the polymerizable monomers may be degassed before addition of a polymerization initiator. Degassing may be performed, for example, by bubbling an inert gas, such as nitrogen gas or argon gas, in the reaction solution for about 0.5 to 5 hours. In degassing, the reaction solution may be heated to about 30° C. to 100° C.

In production of the polymer, any known polymerization initiator in the related art may be used, and examples of polymerization initiators that can be used include, but are not particularly limited to, azo-based polymerization initiators, such as 2,2'-azobisisobutylronitrile, 2,2'-azobis(4-methoxy-2,4-dimethylvaleronitrile), 4,4'-azobis(4-cyanovaleric acid), and 2,2'-azobis(2,4-dimethylvaleronitrile); and redox-type polymerization initiators in which an oxidant, for example, a persulfate, such as potassium persulfate (KPS), sodium persulfate, or ammonium persulfate, or a peroxide, such as hydrogen peroxide, t-butyl peroxide, or methyl ethyl ketone peroxide, is combined with a reductant, for example, sodium sulfite, sodium hydrogen sulfite, or ascorbic acid.

The amount of the polymerization initiator incorporated, based on the total amount (moles) of the polymerizable monomers, is preferably 0.001% to 10% by mole and more preferably 0.001% to 5% by mole.

In addition, depending on the necessity, a chain transfer agent, a polymerization rate modifier, a surfactant, and other additives may also be appropriately used in polymerization.

The atmosphere in the polymerization reaction is not particularly limited, and the polymerization may be performed in the ambient air, or under an atmosphere of an inert gas, such as nitrogen gas or argon gas. In addition, the reaction liquid may be stirred in the polymerization reaction.

The copolymer may precipitate in the polymerization reaction. The copolymer after polymerization can be purified by a common purification method, such as reprecipitation, dialysis, ultrafiltration, or extraction.

The copolymer after purification may be dried by any method, such as lyophilization, vacuum drying, spray drying, or heat drying, but from the viewpoint of small influence on the physical properties of the polymer, lyophilization or vacuum drying is preferable.

The proportion of the structural units derived from each polymerizable monomer in the obtained copolymer can be determined by analyzing peak intensities of groups contained in various structural units using any suitable means such as NMR or IR.

The amount of unreacted monomers contained in the obtained copolymer is preferably 0.01% by weight or less based on the entire copolymer. A smaller amount of unreacted monomers is preferable (lower limit value: 0% by weight). The content of remaining monomers can be measured by any known means, such as high performance liquid chromatography.

<Surface Lubricious Layer (Hydrophilic Polymer)>

The surface lubricious layer in the present disclosure contains a hydrophilic polymer that can be dissolved in a solvent dissolving or swelling the hydrophilic copolymer contained in the adhesive layer. Here, the expression "dissolving the hydrophilic copolymer" means that the hydrophilic copolymer is dissolved at a proportion of 0.01 g/100 g solvent or more (preferably 0.1 g/100 g solvent or more) in a solvent at 23° C. (liquid temperature). In addition, the expression "a hydrophilic polymer that can be dissolved in a solvent" means that the hydrophilic polymer is dissolved at a proportion of 0.01 g/100 g solvent or more (preferably 0.1 g/100 g solvent or more) in a solvent at 23° C. (liquid temperature).

In addition, the solvent dissolves or swells the hydrophilic copolymer contained in the adhesive layer. Specifically, the solvent means a solvent constituting a coating liquid of the hydrophilic copolymer used in forming an adhesive layer. For example, in the following Example 1, a hydrophilic copolymer that can be dissolved in a solvent" means that a hydrophilic polymer is dissolved in methanol/water (7/3 v/v) (liquid temperature: 23° C.) which is a solvent constituting a coating liquid of the hydrophilic polymer at a proportion of 0.01 g/100 g methanol/water (7/3 v/v) or more.

In the present disclosure, as long as the lubricating property (lubricity) and durability (lubrication retaining property) are not affected, another layer may be provided between the surface lubricious layer and the adhesive layer, but the surface lubricious layer is preferably positioned immediately above the adhesive layer. In addition, as long as the lubricating property and durability (lubrication retaining property) are not affected, another layer may be provided on the surface lubricious layer, but another layer is preferably not disposed on the surface lubricious layer (the surface lubricious layer is the outermost layer).

As the solvent, water, a lower alcohol, or a mixed solvent of water and a lower alcohol is preferable. Here, the lower alcohol indicates alcohol having 1 to 3 carbon atoms, that is, methanol, ethanol, n-propanol, or isopropanol.

The hydrophilic polymer is not particularly limited as long as it can be dissolved in water, a lower alcohol, or a mixed solvent of water and a lower alcohol. Such a hydrophilic polymer generally has one or more hydrophilic functional groups, for example, hydroxyl group, amino group, amide group, carboxyl group or salts thereof, phosphonic acid group or salts thereof, phosphate group or salts thereof, sulfonic acid group or salts thereof, sulfuric acid group or salts thereof, sulfurous acid group or salts thereof, twin ion group or salts thereof, and/or ether group. Among them, from the viewpoint of the effect of improving solvent solubility or lubricating property of the hydrophilic polymer in a solvent dissolving or swelling the hydrophilic copolymer contained in the adhesive layer, the hydrophilic polymer preferably has an anionic functional group, more preferably has at least one group selected from the group consisting of sulfonic acid group or salts thereof, sulfuric acid group or salts thereof, and carboxyl group or salts thereof, and particularly preferably has at least one group selected from the group consisting of sulfonic acid group and salts thereof and carboxyl group and salts thereof.

Specific examples of the hydrophilic polymer include polymer electrolyte, polysaccharide, protein, polypeptide, polynucleic acid, non-ionic polymer, and the like.

Examples of the polymer electrolyte include a polymer substance of anionic or anionizable ethylenically unsaturated monomer or salts thereof such as acrylic acid, methacrylic acid, vinyl sulfonic acid, vinyl sulfate, vinyl phosphonate, vinyl phosphate, vinyl boronic acid, citraconic acid, maleic acid, fumaric acid, curonic acid, itaconic acid, methacryloxyethyl phosphate, methacryloxyethyl sulfuric acid, styrene sulfonic acid, methacryloxyethylsulfonic acid and 2-acrylamidemethyl propane sulfonic acid (AMPS), 2-methyl-2-ethyl propanoate-2-phosphate ester (HEMA phosphate), methacryloyloxy PPG-7 phosphate, β-carboxyethyl acrylate, 3-acrylamide-3-methylbutanoic acid, and AMBA polyacrylic acid, polymer substance of amphoteric ethylenically unsaturated monomer such as carboxy betaine (meth)acrylate, carboxy betaine(meth)acrylamide, sulfobetaine(meth)acrylate, sulfobetaine(meth)acrylamide, and phosphobetaine methacrylate (MPC), and the like. Here, the form of the salts is not particularly limited, and examples thereof include alkali metal salts (sodium salt, potassium salt, and the like) of the monomers.

Examples of the polysaccharide include alginic acid, pectin, carrageenan, xanthane, chondroitin sulfate, gum Arabic, guar gum, karaya gum, tragacanth gum, arabinoxylan, heparan sulfate, starch, gum, cellulose derivative, carboxymethyl starch, starch phosphate, hydroxypropyl starch phosphoric acid, starch sulfate, starch-2-hydroxypropyl citric acid, carboxymethyl guar, carboxymethyl hydroxypropyl guar, other anionic galactomannan derivatives, carboxymethyl cellulose, polyanionic cellulose, cellulose sulfate, cellulose polyphosphate, carboxyethyl cellulose, dextran and dextrin, and dextran sulfate and dextrin. These polysaccharides may be in the form of salts. Here, the form of salts is not particularly limited, and examples thereof include alkali metal salts (sodium salt, potassium salt, and the like) of the polysaccharides.

Examples of the polypeptide include polyglutamic acid, polyaspartic acid, and salts thereof. Here, the form of the salts is not particularly limited, and examples thereof include alkali metal salts (sodium salt, potassium salt, and the like) of the polypeptide.

Examples of the non-ionic polymer include polymer substance of non-ionic unsaturated monomer such as vinyl pyrrolidone, vinyl alcohol, dimethyl acrylamide, isopropyl acrylamide, and hydroxyethyl acrylamide, polymer substance of polyol unsaturated monomer such as polyethylene glycol(meth)acrylate, polymer substance of saccharide pendant unsaturated monomer such as 2-methacryloyloxyethyl-D-glycoside and 2-methacryloyloxyethyl-D-mannoside, polyethylene oxide-based polymer substance, water-soluble nylon resin, and derivatives thereof.

Among them, from the viewpoint of the effect of further improving the lubricating property and the binding property with a hydrophilic copolymer (thus durability), the hydrophilic polymer is preferably polymer electrolyte or polysaccharide. That is, the present disclosure provides a medical device including a substrate layer, an adhesive layer, which is formed on at least a portion of the substrate layer, including a hydrophilic copolymer including a structural unit derived from a polymerizable monomer (A) having a sulfobetaine structure, a structural unit derived from a polymerizable monomer (B) having at least one group selected from a sulfonic acid group ($-SO_3H$), a sulfuric acid group ($-OSO_3H$), a sulfurous acid group ($-OSO_2H$), and groups of salts thereof, and a structural unit derived from a polymerizable monomer (C) having a photoreactive group, and a surface lubricious layer, which is formed on at least a portion of the adhesive layer, including at least one hydrophilic polymer selected from the group consisting of a polymer electrolyte and a polysaccharide. In addition, from the viewpoint, the hydrophilic polymer is more preferably a polymer electrolyte or polysaccharide having at least one group selected from the group consisting of a sulfonic acid group and salts thereof, a sulfuric acid group and salts thereof, and carboxyl group and salts thereof, and particularly preferably a polymer electrolyte or polysaccharide having at least one group selected from the group consisting of a sulfonic acid group and salts thereof and carboxyl group and salts thereof.

[Method of Producing Medical Device]

The method of producing the medical device according to the present disclosure is not particularly limited as long as the hydrophilic copolymer is used for the adhesive layer and the hydrophilic polymer is used for the surface lubricious layer, and any known method can be applied as it is or with appropriate modification. For example, a method in which the hydrophilic copolymer is dissolved in a solvent to prepare a coating liquid, which is then applied on a substrate layer of a medical device to form an adhesive layer, and the hydrophilic polymer is dissolved in a solvent to prepare a coating liquid, which is then applied on the substrate layer on which the adhesive layer has been formed in advance to form a surface lubricious layer is preferable. By this method, lubricating property and durability (lubrication retaining property) can be imparted to a surface of a medical device.

(Application Step of Adhesive Layer)

In the method, as a solvent used for dissolving the hydrophilic copolymer, water, a lower alcohol, or a mixed solvent of water and a lower alcohol is preferable from the viewpoint of safety of the operation (for example, low toxicity) and solubility. Here, lower alcohol refers to primary alcohol having 1 to 3 carbon atoms, that is, methanol, ethanol, n-propanol, or isopropanol. The lower alcohol may be used alone or in combination of two or more thereof.

In addition, the concentration of the hydrophilic copolymer in the coating liquid is not particularly limited, and preferably 0.01% to 50% by weight, more preferably 0.05% to 40% by weight, and further more preferably 0.1% to 30% by weight. In these ranges, applicability of the coating liquid is good, and the obtained adhesive layer has sufficient lubricating property and durability (lubrication retaining property). In addition, a uniform adhesive layer having a desired thickness can be easily obtained through a single coating. For this reason, the hydrophilic copolymer can form a strong and uniform chemical bond to the substrate layer by irradiation with an active energy ray (fixing step of adhesive layer) to be described later. In addition, such a concentration is preferable in terms of production efficiency. When the concentration of the hydrophilic copolymer is less than 0.001% by weight, a sufficient amount of hydrophilic copolymer cannot be fixed on a substrate layer surface in some cases. In addition, when the concentration of the hydrophilic copolymer exceeds 20% by weight, the viscosity of the coating liquid may be so high that an adhesive layer having a uniform thickness may not be obtained in some cases. However, a concentration outside the range may be sufficiently applicable to the extent that effects of the present disclosure are not influenced.

The substrate layer surface may be previously subjected to a UV irradiation treatment, a plasma treatment, a corona discharge treatment, a flame treatment, an oxidation treatment, a silane coupling treatment, or a phosphate coupling treatment before application of a coating liquid. When the solvent of a coating liquid is only water, it can be difficult to apply the coating liquid on a hydrophobic substrate layer surface, but a plasma treatment of the substrate layer surface hydrophilizes the substrate layer surface. This can lead to enhancement of wettability of a coating liquid to a substrate layer surface, making it possible to form a uniform adhesive layer. In addition, application of the treatments on a substrate layer surface of a material having no C—H bond, such as a metal or a fluororesin, makes it possible to form a covalent bond to the photoreactive group of the hydrophilic copolymer.

The method of applying a coating liquid to a substrate layer surface is not particularly limited, and any known method in the related art, such as an application/printing method, a dipping method (dipping method, dip-coating method), a spraying method, a spin coating method, or a mixed solution-impregnated sponge coating method can be applied. Among them, a dipping method (dipping method, dip-coating method) is preferable.

(Drying Step of Adhesive Layer)

A substrate layer can be dipped in a coating liquid containing the hydrophilic copolymer of the present disclosure as described above. Then, the substrate layer can be taken out of the coating liquid, and the coating film can be preferably dried. The drying conditions are not particularly limited as long as the drying conditions can remove the solvent from the coating film. For example, a hot air treatment with a dryer or the like or a natural drying may be used. In addition, the pressure condition in drying is also not limited. The drying may be performed at normal pressure (the atmospheric pressure), or at an increased or decreased pressure. As drying means (a device), for example, an oven or a vacuum dryer may be used. In the case of natural drying, no drying device is needed.

(Fixing Step of Adhesive Layer)

The coating film after the drying step can be irradiated with an active energy ray. This can activate the photoreactive group in the coating film (monomer C of hydrophilic copolymer) to form a chemical bond between the photoreactive group and the alkyl group (hydrocarbon group) contained in the substrate layer. More specifically, a description is provided for a case of combination of a photoreactive group having a benzophenone structure and a resin (material having a hydrocarbon group) constituting the substrate layer. When the hydrophilic copolymer contains a photoreactive group having a benzophenone structure, two radicals are generated in the photoreactive group by irradiation with a UV ray. One radical thereof withdraws a hydrogen atom from the alkyl group (hydrocarbon group) in the resin, and instead, one radical is generated on the material. Then, the remaining radical in the photoreactive group is bound to the radical generated on the material, to thereby form a covalent bond between the photoreactive group of the hydrophilic copolymer in the adhesive layer and the material (resin) in the substrate layer. This chemical bond can allow the adhesive layer containing the hydrophilic copolymer to be strongly fixed to the substrate layer. Thus, the adhesive layer can exhibit sufficient durability (lubrication retaining property).

Examples of active energy rays include ultraviolet rays (UV), electron rays, and gamma rays. The active energy ray is preferably a UV ray or an electron ray and, in view of effects on the human body, is more preferably a UV ray. An integrated light quantity (the integrated light quantity of a UV ray on the adhesive layer before applying the surface lubricious layer) of the UV ray when the active energy ray is a UV ray is not particularly limited, but is preferably 100 to 10,000 $mJ/cm^2$, and more preferably 500 to 5,000 $mJ/cm^2$. Examples of the device for the UV ray irradiation can include high pressure mercury lamps, low pressure mercury lamps, metal halide lamps, xenon lamps, and halogen lamps.

After the irradiation with the active energy ray, the coating film may be washed with a solvent (for example, a solvent used in preparing a coating liquid) to remove the unreacted hydrophilic copolymer.

The fixation of the coating film (adhesive layer) onto the substrate layer can be checked using known analysis means, such as FT-IR or XPS. For example, the fixation can be checked by comparing the ratio of a peak of a bond formed through the irradiation with the active energy ray and a peak of an unchanged bond using FT-IR measurement before and after the irradiation with an active energy ray.

By the method, in the medical device according to the present disclosure, an adhesive layer containing the hydrophilic copolymer is formed on a surface of the substrate layer.

(Application Step of Surface Lubricious Layer)

Here, the hydrophilic polymer is dissolved in a solvent to prepare a coating liquid, and the coating liquid is applied on the adhesive layer formed as described above. In the method, as a solvent used for dissolving the hydrophilic polymer, water, a lower alcohol, or a mixed solvent of water and a lower alcohol is preferable from the viewpoint of safety of the operation (low toxicity) and solubility. Here, lower alcohol refers to primary alcohol having 1 to 3 carbon atoms, that is, methanol, ethanol, n-propanol, or isopropanol. The lower alcohol may be used alone or used in combination of two or more thereof.

In addition, the concentration of the hydrophilic polymer in the coating liquid is not particularly limited, and is preferably 0.01% to 50% by weight, more preferably 0.05% to 40% by weight, and further more preferably 0.1% to 30% by weight. In these ranges, applicability of the coating liquid is good, and the obtained surface lubricious layer is superior in the lubricating property and durability (lubrication retaining property). In addition, a uniform surface lubricious layer having a desired thickness can be easily obtained through a single coating. For this reason, the hydrophilic copolymer can form a strong and uniform chemical bond to the surface lubricious layer (hydrophilic polymer) by irradiation (fixation step of surface lubricious layer) with an active energy ray to be described later. In addition, such a concentration is preferable in terms of production efficiency. When the concentration of the hydrophilic polymer is less than 0.001% by weight, a sufficient amount of the hydrophilic polymer may not be fixed on an adhesive layer surface in some cases. In addition, when the concentration of the hydrophilic polymer exceeds 20% by weight, the viscosity of the coating liquid may be so high that a surface lubricious layer having a uniform thickness may not be obtained in some cases. However, a concentration outside the range may be sufficiently applicable to the extent that the effects of the present disclosure are not influenced.

The method of applying a coating liquid to an adhesive layer surface is not particularly limited, and any known method in the related art, such as an application/printing method a dipping method (dipping method, dip-coating method), a spraying method, a spin coating method, or a mixed solution-impregnated sponge coating method can be applied. Among them, a dipping method (dipping method, dip-coating method) is preferable.

(Drying Step of Surface Lubricious Layer)

A substrate layer on which an adhesive layer has been formed in advance can be dipped in a coating liquid containing the hydrophilic polymer. Then, the substrate layer can be taken out of the coating liquid, and the coating film can be preferably dried. The drying conditions are not particularly limited as long as the drying conditions can remove the solvent from the coating film. For example, a hot air treatment with a dryer or the like or a natural drying may be used. In addition, the pressure condition in drying is also not limited. The drying may be performed at normal pressure (the atmospheric pressure), or at an increased or decreased pressure. As drying means (a device), for example, an oven or a vacuum dryer may be used. In the case of natural drying, no drying device is needed.

(Fixation Step of Surface Lubricious Layer)

The coating film after the drying step can be irradiated with an active energy ray. This can activate the unreacted photoreactive group in the adhesive layer (monomer C of hydrophilic copolymer) to form a chemical bond between the photoreactive group and the alkyl group (hydrocarbon group) contained in the hydrophilic polymer. More specifically, a description is provided for a case of combination of a photoreactive group having a benzophenone structure of the hydrophilic copolymer in the adhesive layer and the surface lubricious layer (hydrophilic polymer). When the hydrophilic copolymer contains a photoreactive group having a benzophenone structure, two radicals are generated in the photoreactive group by irradiation with a UV ray. One radical thereof withdraws a hydrogen atom from the alkyl group (hydrocarbon group) in the hydrophilic polymer, and instead, one radical is generated on the hydrophilic polymer. Then, the remaining radical in the photoreactive group is bound to the radical of the hydrophilic polymer to thereby form a covalent bond between the photoreactive group of the hydrophilic copolymer in the adhesive layer and the hydrophilic polymer in the surface lubricious layer. This chemical bond can allow the surface lubricious layer containing the hydrophilic polymer to be strongly fixed to the adhesive layer. Thus, the surface lubricious layer can exhibit superior durability (lubrication retaining property).

Examples of active energy rays include ultraviolet rays, electron rays, and gamma rays. The active energy ray is preferably a UV ray or an electron ray, and in view of effects on the human body, is more preferably a UV ray. An integrated light quantity (the integrated light quantity of a UV ray on the surface lubricious layer) of the UV ray when the active energy ray is a UV ray is not particularly limited, but is preferably 500 to 90,000 mJ/cm$^2$, more preferably 900 to 65,000 mJ/cm$^2$, and further more preferably 1,400 to 40,000 mJ/cm$^2$. In addition, the integrated light quantity of a UV ray on the adhesive layer after applying the surface lubricious layer is not particularly limited, but is preferably 600 to 100,000 mJ/cm$^2$, more preferably 1,000 to 75,000 mJ/cm$^2$, and further more preferably 1,500 to 50,000 mJ/cm$^2$. "Integrated light quantity of a UV ray on the adhesive layer after applying the surface lubricious layer" means a total value of the integrated light quantity of a UV ray on the adhesive layer and the integrated light quantity of a UV ray on the surface lubricious layer. Examples of devices for the UV ray irradiation include high pressure mercury lamps, low pressure mercury lamps, metal halide lamps, xenon lamps, and halogen lamps.

After the irradiation with the active energy ray, the coating film may be washed with a solvent (for example, a solvent used in preparing a coating liquid) to remove the unreacted hydrophilic copolymer.

The fixation of the coating film (surface lubricious layer) onto the adhesive layer can be checked using known analysis means, such as FT-IR or XPS. For example, the fixation can be checked by comparing the ratio of a peak of a bond formed through the irradiation with the active energy ray and a peak of an unchanged bond using FT-IR measurement before and after the irradiation with an active energy ray.

By the method described above, in embodiments of a medical device described herein, a surface lubricious layer containing the hydrophilic polymer is formed on a surface of the adhesive layer.

[Use of Medical Device]

The medical device 10 can be used in contact with body fluid or blood. The surface can have a lubricating property in an aqueous solution such as body fluid or a saline, being capable of enhancing operability and reducing damage of tissue mucosa. Specific examples include catheters, stents, and guide wires used in blood vessels. That is, in certain embodiments, the medical device is a catheter, a stent, or a guide wire.

A medical device described herein is exemplified by the following non-limiting embodiments:

(a) Catheters to be orally or nasally inserted or allowed to indwell in a digestive organ, such as stomach tube catheters, digestive catheters, and tubes for enteric nutrients.

(b) Catheters to be orally or nasally inserted or allowed to indwell in a respiratory tract or trachea, such as oxygen catheters, oxygen cannulas, tubes and cuffs of tracheal tubes, tubes and cuffs of tracheotomy tubes, and tracheal aspiration catheters.

(c) Catheters to be inserted or allowed to indwell in a urethra or ureter, such as urethra catheters, urinary catheters, and catheters and balloons of urethra balloon catheters.

(d) Catheters to be inserted or allowed to indwell in various lumens in living bodies, organs, and tissues, such as suction catheters, drain catheters, and rectum catheters.

(e) Catheters to be inserted or allowed to indwell in a blood vessel, such as indwelling needles, IVH catheters, thermodilution catheters, angiography catheters, vasodilation catheters, and dilators or introducers, or guide wires, stylets, and the like for the catheters.

(f) Artificial tracheae, artificial bronchi, and the like.

(g) Medical devices for extracorporeal circulation therapy (artificial lungs, artificial hearts, artificial kidneys, and the like) and circuits therefore.

EXAMPLES

Hereinafter, embodiments described herein will be described specifically below with respect to examples. However, the medical devices and methods for producing medical devices described herein are not limited to the particular embodiments described in the examples. The parts and % (percentages) in the examples are all by weight. In the following examples, unless otherwise defined, the conditions for allowing to stand at room temperature are all at 23° C./55% RH.

<Production of Copolymer>

1.40 g (5.0 mmol) of [2-(methacryloyloxy)ethyl]dimethyl-(3-sulfopropyl)ammonium hydroxide (MSPB) manufactured by Sigma-Aldrich, 1.83 g (4.0 mmol) of 2-acrylamide-2-methyl-1-propanesulfonic acid sodium salt (AMPS (Na) 50 wt % aqueous solution manufactured by Sigma-Aldrich, and 0.266 g (1.0 mmol) of 4-methacryloyloxybenzophenone (MBP) manufactured by MRC UNITEC Co., Ltd were dissolved in 10 mL of a 2,2,2-trifluoroethanol/water (8/2 v/v) mixed solvent to prepare a reaction solution. Next, the reaction solution was put in a 30 mL eggplant-shaped flask, oxygen was removed by sufficient nitrogen bubbling, 2.8 mg (0.010 mmol) of a polymerization initiator 4,4'-azobis(4-cyanovaleric acid) was added, followed by immediate sealing, and polymerization was carried out in a water bath at 75° C. for 3 hours. Next, the solvent was subjected to reprecipitation in acetone, and the supernatant was removed by decantation to obtain a copolymer.

The composition of the obtained copolymer was MSPB: AMPS (Na):MPB=50:40:10 in terms of mole %. Here, the obtained copolymer corresponds to a hydrophilic copolymer contained in the adhesive layer according to the present disclosure. In addition, a weight average molecular weight (Mw) of the obtained copolymer was measured by gel permeation chromatography (GPC), which was 110,000.

Example 1

The obtained copolymer (corresponding to the hydrophilic copolymer according to the present disclosure) was dissolved in methanol/water (7/3 v/v) so as to be 10% by weight, to prepare a coating liquid. Next, a polyamide tube (having an outer diameter of 2.4 mm and a length of 70 mm) was dipped in the coating liquid, and withdrawn at a rate of 15 mm/sec. Next, the polyamide tube was dried with a dryer for 30 seconds to remove the solvent. Next, the polyamide tube was irradiated with an ultraviolet ray (UV) having a wavelength of 365 nm and a lamp power of 1 kW under conditions of an irradiation distance of 200 mm and a sample transporting rate of 2 m/min (integrated light quantity: 1,000 mJ/cm2). As for the UV irradiation device, UVC-1212/ IMNLC3-AA04 (high pressure mercury lamp) of Ushio Inc. was used. Next, sodium polystyrene sulfonate (corresponding to the hydrophilic polymer according to the present invention) manufactured by Sigma-Aldrich was dissolved in methanol/water (5/5 v/v) so as to be 5% by weight to prepare a coating liquid. Next, the polyamide tube which has just been coated with the hydrophilic copolymer was dipped in the coating liquid, and withdrawn at a rate of 5 mm/sec. Next, the polyamide tube was dried with a dryer for 30 seconds to remove the solvent. Next, the polyamide tube was irradiated with UV having a wavelength of 365 nm and a lamp power of 1 kW under conditions of an irradiation distance of 200 mm and a sample transporting rate of 2 m/min (integrated light quantity: 9,000 mJ/cm2) to obtain a sample. As for a UV irradiation device, UVC-1212/ 1MNLC3-AA04 (high pressure mercury lamp) of Ushio Inc. was used.

Sodium polystyrene sulfonate was dissolved in methanol/water (7/3 v/v) (liquid temperature: 23° C.) at a proportion of 0.1 g/100 g methanol/water (7/3 v/v) or more. The sodium polystyrene sulfonate was not dissolved in acetone (liquid temperature: 23° C.) (solubility: less than 0.01 g/100 g acetone).

Figure 3:
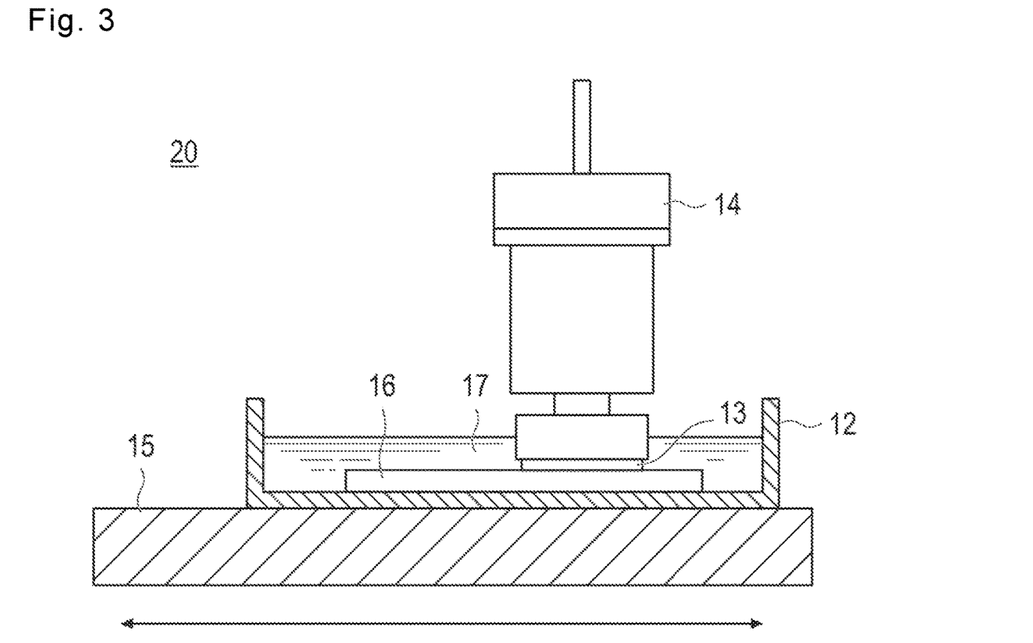
FIG. 3 is a schematic diagram of a lubricating property and durability testing device (friction meter) used in Examples 1 to 3 and Comparative Example 1.

Next, the obtained sample was evaluated for the lubricating property and durability (lubrication retaining property) using a friction meter (Handy Tribo Master TL201 manufactured by Trinity-Lab Inc.) 20 shown in FIG. 3 according to the following method.

Figure 4:
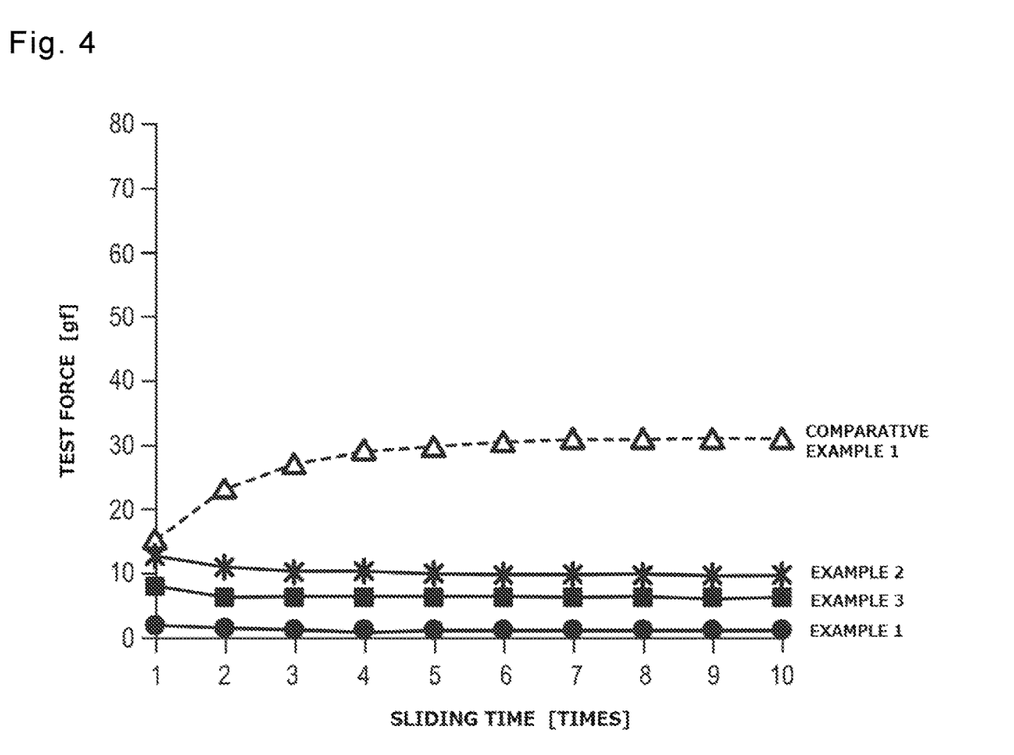
FIG. 4 is a figure showing results of the lubricating property and durability test in Examples 1 to 3 and Comparative Example 1.

The sample 16 was fixed in a petri dish 12, and was dipped in physiological saline water (physiological saline solution) 17 having such a depth that the entire sample 16 was soaked in the physiological saline water. The petri dish 12 was placed on a moving table 15 of the friction meter 20 shown in FIG. 3. An HDPE terminal ($\phi$ 10 mm, R[1] mm) 13 was brought into contact with the polyamide tube, and a load 14 of 450 g was applied on the terminal. While the moving table 15 was subjected to 10 horizontal reciprocations under a sliding distance set to 20 mm and a sliding speed set to 16.7 mm/sec, the sliding resistance (gf) was measured. During the reciprocations from the first time to $10^{th}$ time, an average of the sliding resistance for each reciprocation was taken and plotted on a graph, as depicted in FIG. 4, as a test force to thereby evaluate the variation of the sliding resistance during the 10 repeated slides.

Example 2

Production of the sample and measurement of sliding resistance were performed in the same manner as in Example 1 except for using chondroitin sulfate C sodium salt manufactured by Waco Pure Chemical Corporation in place of sodium polystyrene sulfonate. Chondroitin sulfate C sodium salt was dissolved in methanol/water (7/3 v/v) (liquid temperature: 23° C.) at a proportion of 0.1 g/100 g methanol/water (7/3 v/v) or more. The chondroitin sulfate C sodium salt was not dissolved in acetone (liquid temperature: 23° C.) (solubility: less than 0.01 g/100 g acetone).

Example 3

The obtained copolymer (corresponding to the hydrophilic copolymer according to the present disclosure) was dissolved in methanol/water (7/3 v/v) so as to be 10% by weight to prepare a coating liquid. Next, the polyamide tube (having an outer diameter of 2.4 mm and a length of 70 mm) was dipped in the coating liquid, and withdrawn at a rate of 15 mm/sec. Next, the polyamide tube was dried with a dryer for 30 seconds to remove the solvent. Next, the polyamide tube was irradiated with an ultraviolet ray (UV) having a wavelength of 365 nm and a lamp power of 1 kW under conditions of an irradiation distance of 200 mm and a sample transporting rate of 2 m/min (integrated light quantity: 1,000 mJ/cm2). As for a UV irradiation device, UVC-1212/1MNLC3-AA04 (high pressure mercury lamp) of Ushio Inc. was used. Next, carboxymethyl cellulose sodium salt (corresponding to the hydrophilic polymer according to the present disclosure) manufactured by Sigma-Aldrich was dissolved in methanol/water (5/5 v/v) so as to be 0.1% by weight to prepare a coating liquid. Next, the polyamide tube which has just been coated with the hydrophilic copolymer was dipped in the coating liquid, and withdrawn at a rate of 5 mm/sec. Next, the polyamide tube was dried with a drier for 30 seconds to remove the solvent. Next, the polyamide tube was irradiated with UV having a wavelength of 365 nm and a lamp power of 1 kW under conditions of an irradiation distance of 200 mm and a sample transporting rate of 2 m/min (integrated light quantity: 9,000 mJ/cm2) to obtain a sample. As for a UV irradiation device, UVC-1212/1MNLC3-AA04 (high pressure mercury lamp) of Ushio Inc. was used.

Carboxymethyl cellulose sodium salt was dissolved in methanol/water (7/3 v/v) (liquid temperature: 23° C.) at a proportion of 0.1 g/100 g methanol/water (7/3 v/v) or more. The carboxymethyl cellulose sodium salt was not dissolved in acetone (liquid temperature: 23° C.) (solubility: less than 0.01 g/100 g acetone).

Next, the obtained sample was measured for the sliding resistance in the same manner as in Example 1. See FIG. 4.

Comparative Example 1

Production of the sample and measurement of sliding resistance were performed in the same manner as in Example 1 except for using a block copolymer of N,N-dimethyl acrylamide and glycidyl methacrylate in place of sodium polystyrene sulfonate and using acetone in place of methanol/water (5/5 v/v) as a solvent dissolving the block copolymer of N,N-dimethyl acrylamide and glycidyl methacrylate. The block copolymer of N,N-dimethyl acrylamide and glycidyl methacrylate was not dissolved in methanol/water (7/3 v/v) (liquid temperature: 23° C.) (solubility: less than 0.01 g/100 g methanol/water (7/3 v/v). Rather, the block copolymer of N,N-dimethyl acrylamide and glycidyl methacrylate was dissolved in acetone (liquid temperature: 23° C.) at a proportion of 0.1 g/100 g acetone or more.

In addition, the obtained copolymer (corresponding to the hydrophilic copolymer according to the present disclosure) was not dissolved in acetone (liquid temperature: 23° C.) (solubility: less than 0.01 g/100 g acetone).

The block copolymer of N,N-dimethyl acrylamide and glycidyl methacrylate used in the present example was produced according to the following method.

That is, 29.7 g of triethylene glycol was dropped in 72.3 g of adipic acid dichloride while the adipic acid dichloride was at a temperature of 50° C., and then hydrochloric acid was removed under reduced pressure at 50° C. for 3 hours to obtain oligoester. Next, 4.5 g of methylethylketone was added to 22.5 g of the obtained oligoester, and this was dropped in a solution formed of 5 g of sodium hydroxide, 6.93 g of 31% hydrogen peroxide, 0.44 g of dioctyl phosphate as a surfactant, and 120 g of water, and reacted at −5° C. for 20 minutes. The obtained product was repeatedly washed with water and with methanol, and then dried to obtain a polyperoxide (PPO) having a plurality of peroxide groups per molecule.

Next, 0.5 g of the PPO and 9.5 g of glycidyl methacrylate (GMA) were polymerized while stirring at 80° C. under reduced pressure for 2 hours using 30 g of benzene as a solvent. The obtained reaction product after polymerization was subjected to reprecipitation in diethyl ether to obtain polyglycidyl methacrylate (PPO-GMA) having a plurality of peroxide groups per molecule.

Subsequently, 1.0 g of the obtained PPO-GMA (7 mmol as GMA) was supplied in 9.0 g of dimethyl acrylamide (DMAA) and 90 g of dimethyl sulfoxide as a solvent and reacted at 80° C. for 18 hours. The reaction product obtained after reaction was subjected to reprecipitation in hexane and recovered to obtain a block copolymer (structural unit (A): structural unit (B)=GMA:DMAA=1:14 (molar ratio)) having an epoxy group in molecule and exhibiting lubricating property during wetting. By analyzing the block copolymer obtained in this manner by NMR and ATR-IR, it was checked that an epoxy group was present. In addition, a weight average molecular weight (Mw) of the block copolymer measured by gel permeation chromatography (GPC, in terms of polystyrene) was about 1.5 million.

The results of Examples 1 to 3 and Comparative Example 1 are shown in FIG. 4. The samples of Examples 1 to 3 had significantly low sliding values as compared with the sample of Comparative Example 1. In addition, while the sliding resistance of Comparative Example 1 increased, the samples of Examples 1 to 3 did not present such a phenomenon that the sliding resistance increases as the sliding time increases. From this, it is estimated that acetone which is a solvent of Comparative Example 1 does not dissolve or swell the hydrophilic copolymer, and thus the surface lubricious layer cannot interact with the adhesive layer, and thereby cannot obtain sufficient adhesiveness.

Additionally, the sample of Comparative Example 1 had a higher sliding resistance compared with the initial sliding resistance, and thus retained sufficient lubricating property and durability (lubrication retaining property). From this, it is estimated that the surface lubricious layer is exfoliated and the adhesive layer is exposed, whereas the adhesive layer itself has lubricating property and durability (lubrication retaining property). From this, it is suggested that the adhesive layer formed by using the hydrophilic copolymer according to the present disclosure has superior adhesiveness to the surface lubricious layer, and the adhesive layer itself exhibits sufficient lubricating property and durability (lubrication retaining property).

The detailed description above describes embodiments of a medical device and fabrication method representing examples of the inventive medical device and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST

1 Substrate layer
1a Substrate layer core portion
1b Substrate surface layer
2 Adhesive layer
3 Surface lubricious layer
10 Medical device
12 Petri dish
13 HDPE terminal
14 Load
15 Moving table
16 Polyamide tube (sample)
17 Physiological saline water
20 Friction meter

What is claimed is:

1. A medical device comprising:
a substrate layer;
an adhesive layer, which is formed on at least a portion of the substrate layer, the adhesive layer comprising a hydrophilic copolymer comprising a structural unit derived from a polymerizable monomer (A) having a sulfobetaine structure, a structural unit derived from a polymerizable monomer (B) having at least one group selected from the group consisting of a sulfonic acid group (—$SO_3H$), a sulfuric acid group (—$OSO_3H$), a sulfurous acid group (—$OSO_2H$), and salts thereof, and a structural unit derived from a polymerizable monomer (C) having a photoreactive group; and
a surface lubricious layer, which is formed on at least a portion of the adhesive layer, the surface lubricious layer comprising a hydrophilic polymer which is dissolvable in a solvent that dissolves or swells the hydrophilic copolymer.

2. The medical device according to claim 1, wherein the solvent is water, a lower alcohol, or a mixed solvent comprising water and a lower alcohol.

3. The medical device according to claim 1, wherein the hydrophilic polymer is a polymer electrolyte or polysaccharide.

4. The medical device according to claim 1, wherein the polymerizable monomer (A) is represented by formula (1):

wherein
$R^{11}$ is a hydrogen atom or a methyl group,
$Z^1$ is an oxygen atom or —NH—,
$R^{12}$ and $R^{15}$ are each independently a straight chain or branched chain alkylene group having 1 to 20 carbon atoms, and
$R^{13}$ and $R^{14}$ are each independently a straight chain or branched chain alkyl group having 1 to 20 carbon atoms.

5. The medical device according to claim 1, wherein the polymerizable monomer (B) is represented by formula (2):

wherein
$R^{21}$ is a hydrogen atom or a methyl group,
$Z^2$ is an oxygen atom or —NH—,
$R^{22}$ is a straight chain or branched chain alkylene group having 1 to 20 carbon atoms, and
X is a group selected from the group consisting of a sulfonic acid group (—$SO_3H$), a sulfuric acid group (—$OSO_3H$), a sulfurous acid group (—$OSO_2H$), and salts thereof;
or wherein the polymerizable monomer (B) is represented by formula (3):

wherein
$R^{31}$ is a hydrogen atom or a methyl group,
$R^{32}$ is a straight chain or branched chain alkylene group having 1 to 20 carbon atoms, X is a group selected from the group consisting of a sulfonic acid group (—SO₃H), a sulfuric acid group (—OSO₃H), a sulfurous acid group (—OSO₂H), and salts thereof;

or wherein the polymerizable monomer (B) is represented by formula (4):

(4)

wherein

R⁴¹ is a hydrogen atom or a methyl group,

R⁴² is a straight chain or branched chain alkylene group having 1 to 20 carbon atoms, and

X is a group selected from the group consisting of a sulfonic acid group (—SO₃H), a sulfuric acid group (—OSO₃H), a sulfurous acid group (—OSO₂H), and salts thereof.

6. The medical device according to any claim 1 wherein the medical device is a catheter, a stent, or a guide wire.

7. The medical device according to claim 1, wherein the photoreactive group is an azide group, a diazo group, a diazirine group, a ketone group, or a quinone group.

8. The medical device according to claim 1, wherein the adhesive layer and substrate layer are in immediate contact.

9. The medical device according to claim 1, wherein the polymerizable monomer (B) is represented by formula (2):

(2)

wherein

R²¹ is a hydrogen atom or a methyl group,

Z² is —NH—,

R²² is a straight chain or branched chain alkylene group having 1 to 12 carbon atoms, and X is a group selected from the group consisting of a sulfonic acid group, a sulfuric acid group, and salts thereof.

10. A medical device comprising:

a substrate layer;

an adhesive layer, which is formed on at least a portion of the substrate layer, the adhesive layer comprising a hydrophilic copolymer comprising a structural unit derived from a polymerizable monomer (A) having a sulfobetaine structure, a structural unit derived from a polymerizable monomer (B) having at least one group selected from the group consisting of a sulfonic acid group (—SO₃H), a sulfuric acid group (—OSO₃H), a sulfurous acid group (—OSO₂H), and salts thereof, and a structural unit derived from a polymerizable monomer (C) having a photoreactive group; and a surface lubricious layer, which is formed on at least a portion of the adhesive layer, the surface lubricious layer comprising at least one hydrophilic polymer selected from the group consisting of a polymer electrolyte and a polysaccharide.

11. The medical device according to claim 10, wherein the polymerizable monomer (A) is represented by formula (1):

(1)

wherein

R¹¹ is a hydrogen atom or a methyl group,

Z¹ is an oxygen atom or —NH—,

R¹² and R¹⁵ are each independently a straight chain or branched chain alkylene group having 1 to 20 carbon atoms, and R¹³ and R¹⁴ are each independently a straight chain or branched chain alkyl group having 1 to 20 carbon atoms.

12. The medical device according to claim 10, wherein the polymerizable monomer (B) is represented by formula (2):

(2)

wherein

R²¹ is a hydrogen atom or a methyl group,

Z² is an oxygen atom or —NH—,

R²² is a straight chain or branched chain alkylene group having 1 to 20 carbon atoms, and X is a group selected from the group consisting of a sulfonic acid group (—SO₃H), a sulfuric acid group (—OSO₃H), a sulfurous acid group (—OSO₂H), and salts thereof;

or wherein the polymerizable monomer (B) is represented by formula (3):

(3)

wherein $R^{31}$ is a hydrogen atom or a methyl group, $R^{32}$ is a single bond or a straight chain or branched chain alkylene group having 1 to 20 carbon atoms, and X is a group selected from the group consisting of a sulfonic acid group ($-SO_3H$), a sulfuric acid group ($-OSO_3H$), a sulfurous acid group ($-OSO_2H$), and salts thereof;

or wherein the polymerizable monomer (B) is represented by formula (4):

(4)

wherein $R^{41}$ is a hydrogen atom or a methyl group, $R^{42}$ is a straight chain or branched chain alkylene group having 1 to 20 carbon atoms, and

X is a group selected from the group consisting of a sulfonic acid group ($-SO_3H$), a sulfuric acid group ($-OSO_3H$), a sulfurous acid group ($-OSO_2H$), and salts thereof.

13. The medical device according to claim 10, wherein the medical device is a catheter, a stent, or a guide wire.

14. The medical device according to claim 10, wherein the photoreactive group is an azide group, a diazo group, a diazirine group, a ketone group, or a quinone group.

15. The medical device according to claim 10, wherein the adhesive layer and substrate layer are in immediate contact.

16. The medical device according to claim 10, wherein the polymerizable monomer (B) is represented by formula (2):

(2)

wherein $R^{21}$ is a hydrogen atom or a methyl group, $Z^2$ is $-NH-$, $R^{22}$ is a straight chain or branched chain alkylene group having 1 to 12 carbon atoms, and X is a group selected from the group consisting of a sulfonic acid group, a sulfuric acid group, and salts thereof.

17. A method for producing a medical device, the method comprising:

dissolving a hydrophilic copolymer in a first solvent to prepare a first coating liquid;

dissolving a hydrophilic polymer in a second solvent to prepare a second coating liquid;

applying the first coating liquid to a surface of a substrate layer of a medical device to form an adhesive layer on the substrate layer;

fixing the adhesive layer to the substrate layer via irradiation with ultraviolet rays, electron rays, or gamma rays;

applying the second coating liquid to the adhesive layer after the fixing of the adhesive layer to form a surface lubricious layer; and fixing the surface lubricious layer to the substrate layer via irradiation with ultraviolet rays, electron rays, or gamma rays, wherein the hydrophilic copolymer comprises a structural unit derived from a polymerizable monomer (A) having a sulfobetaine structure, a structural unit derived from a polymerizable monomer (B) having at least one group selected from the group consisting of a sulfonic acid group ($-SO_3H$), a sulfuric acid group ($-OSO_3H$), a sulfurous acid group ($-OSO_2H$), and salts thereof, and a structural unit derived from a polymerizable monomer (C) having a photoreactive group; and wherein the first and second solvents are each independently selected from the group consisting of water, a lower alcohol, and a mixed solvent of water and a lower alcohol.

18. The method according to claim 17, wherein the first and second solvents are both mixed solvents of water and a lower alcohol.

19. The method according to claim 17, wherein the polymerizable monomer (A) is represented by formula (1):

(1)

wherein $R^{11}$ is a hydrogen atom or a methyl group, $Z^1$ is an oxygen atom or $-NH-$, $R^{12}$ and $R^{15}$ are each independently a straight chain or branched chain alkylene group having 1 to 20 carbon atoms, and $R^{13}$ and $R^{14}$ are each independently a straight chain or branched chain alkyl group having 1 to 20 carbon atoms.

20. The method according to claim 17, wherein the polymerizable monomer (B) is represented by formula (2):

$$\begin{array}{c} R^{21} \\ | \\ H_2C=C \\ | \\ C=O \\ | \\ Z^2 \\ | \\ R^{22} \\ | \\ X \end{array} \quad (2)$$

wherein
$R^{21}$ is a hydrogen atom or a methyl group,
$Z^2$ is an oxygen atom or —NH—,
$R^{22}$ is a straight chain or branched chain alkylene group having 1 to 20 carbon atoms, and
X is a group selected from the group consisting of a sulfonic acid group (—SO$_3$H), a sulfuric acid group (—OSO$_3$H), a sulfurous acid group (—OSO$_2$H), and salts thereof;
or wherein the polymerizable monomer (B) is represented by formula (3):

$$\begin{array}{c} R^{31} \\ | \\ H_2C=C \\ | \\ R^{32} \\ | \\ X \end{array} \quad (3)$$

wherein
$R^{31}$ is a hydrogen atom or a methyl group,
$R^{32}$ is a straight chain or branched chain alkylene group having 1 to 20 carbon atoms,
X is a group selected from the group consisting of a sulfonic acid group (—SO$_3$H), a sulfuric acid group (—OSO$_3$H), a sulfurous acid group (—OSO$_2$H), and salts thereof;
or wherein the polymerizable monomer (B) is represented by formula (4):

$$\begin{array}{c} R^{41} \\ | \\ H_2C=C \\ | \\ O \\ | \\ R^{42} \\ | \\ X \end{array} \quad (4)$$

wherein
$R^{41}$ is a hydrogen atom or a methyl group,
$R^{42}$ is a straight chain or branched chain alkylene group having 1 to 20 carbon atoms, and
X is a group selected from the group consisting of a sulfonic acid group (—SO$_3$H), a sulfuric acid group (—OSO$_3$H), a sulfurous acid group (—OSO$_2$H), and salts thereof.

\* \* \* \* \*